(12) United States Patent
Baillon et al.

(10) Patent No.: US 7,700,141 B2
(45) Date of Patent: *Apr. 20, 2010

(54) COMPOSITION

(75) Inventors: Marie-Louise Baillon, Leicestershire (GB); Marinus Pannevis, Verden (DE); Thomas Brenten, Verden (DE)

(73) Assignee: Mars Incorporated, McLean, VA (US)

( * ) Notice: Subject to any disclaimer, the term of this patent is extended or adjusted under 35 U.S.C. 154(b) by 515 days.

This patent is subject to a terminal disclaimer.

(21) Appl. No.: 11/522,721

(22) Filed: Sep. 18, 2006

(65) Prior Publication Data

US 2007/0202087 A1    Aug. 30, 2007

(30) Foreign Application Priority Data

Sep. 20, 2005    (GB)    ................... 0519164.8

(51) Int. Cl.
*A23K 1/18*    (2006.01)
*A61K 47/00*    (2006.01)

(52) U.S. Cl. .............. 426/61; 426/805; 426/2; 424/93.45

(58) Field of Classification Search .......... 426/61, 426/805, 2; 424/93.45
See application file for complete search history.

(56) References Cited

FOREIGN PATENT DOCUMENTS

| WO | WO-03/041512 | 5/2003 |
|---|---|---|
| WO | WO-2005/060707 | 7/2005 |
| WO | WO-2005/060708 | 7/2005 |
| WO | WO-2005/092116 | 10/2005 |

OTHER PUBLICATIONS

Baillon, PhD, Marie-Louise A., Zoe V. Marshall-Jones, PhD, Richard F. Butterwick, PhD. Effects of probiotic *Lactobacillus acidophilus* strain DSM 13241 in healthy adult dogs, AJVR, vol. 65, No. 3, Mar. 2004, pp. 338-343.
BSI Congress 2000, Comparative immunology, p. 110.
AGAA 1357, Apr. 2000, Entries 6177-6180.
Waltham International Symposium: Pet Nutrition Coming of Age; Zentek, et al; Aug. 607, 2001.
Food sensitivity in the dog: a quantitative study; C. J. Chesney; Hournal of Small Animal Practice (2002) 43, 203-207.
Zentek et al., "Dietary Protein Source and Manufacturing Processes Affect Macronutrient Digestibility, Fecal Consistency, and Presence of Fecal Clostridium perfringens in Adult Dogs", J. Nutr. 134:2158S-2161S, Aug. 2004.
Zentek et al., "Morphology and Immunopathology of the Small and Large Intestine in Dogs with Nonspecific Dietary Sensitivity", J. Nutr. 132:1652S-1654S, Jun. 2002.

*Primary Examiner*—C. Sayala
(74) *Attorney, Agent, or Firm*—Fulbright & Jaworski LLP

(57) ABSTRACT

The present invention provides the use of the probiotic micro organism deposited under the accession number NCIMB 41117, in the manufacture of a composition for the treatment of non specific dietary sensitivity in a dog or a cat. The present invention also provides a method for the treatment of non specific dietary sensitivity in a dog or a cat, the method comprising administering to the dog or cat the probiotic micro organism deposited under the accession number NCIMB 41117.

5 Claims, 1 Drawing Sheet

COMPOSITION

CROSS-REFERENCE TO RELATED APPLICATIONS

This application claims priority Great Britain Application No. GB 0519164.8 filed Sep. 20, 2005.

TECHNICAL FIELD

The present invention provides the use of the probiotic micro organism deposited under the accession number NCIMB 41117, in the manufacture of a composition for the treatment of non specific dietary sensitivity in a dog or a cat. The present invention also provides a method for the treatment of non specific dietary sensitivity in a dog or a cat, the method comprising administering to the dog or cat the probiotic micro organism deposited under the accession number NCIMB 41117.

BACKGROUND OF THE INVENTION

Probiotics have long been used in the nutrition of domestic animals. Different indications have been given for their use in the companion animals dogs and cats. Non-specific sensitivity (NSS), in dogs or cats, can occur in response to certain feed ingredients or in response to specific types of diets. It is characterized by soft fecal consistency. NSS is a recognised pathological condition in dogs and cats and can be defined as an intestinal disorder, characterized by the production of unformed wet feces, without further health impairment. The etiology of the condition is unclear, although the problem is related to dietary factors. It does not, however, seem to be limited to a specific ingredient. Loose fecal consistency can, for example, be reproduced by feeding commercial or home-cooked diets containing higher concentrations of animal derived protein sources. The problem may be associated with a reduction in colonic absorptive function, given that water, sodium and chloride absorption is lower and potassium secretion higher compared to that of unaffected individuals. Canned commercial diets are more problematical compared to dry kibble based pet food in NSS. A direct effect by dietary components on the gut wall or a disruption of the intestinal physiology with consequent impacts on absorptive intestinal function are potential causes of the disorder. Because little is known about the cause of NSS in dogs or cats, probiotics have not previously been thought useful to address this disorder.

BRIEF SUMMARY OF THE INVENTION

The present invention relates to the use of the probiotic micro-organism deposited on 10 Oct. 2001 under the accession number NCIMB 41117 in the manufacture of a composition for the treatment of NSS in a dog or a cat.

The micro-organism was deposited with the depository institution NCIMB Ltd, 23 St Machar Drive, Aberdeen, AB24 3RY, Scotland, in accordance with the Budapest Treaty on the International Recognition of the Deposit of Micro-organisms for the purposes of patent procedure.

*Lactobacillus acidophillus* deposited under the accession number NCIMB 41117 is a Gram-positive, catalase-negative, non-sporulating bacillus. Microscopically, the cultures are non-motile rods, varying in size from short rods to long filaments. These organisms are from the family of lactic acid bacteria, which refers to the characteristic acid production during metabolic growth.

Lactobacilli are cultured under anaerobic or microaerophilic conditions on selective media such as MRS and M17 agar. Growth of these organisms into defined visible colonies on agar plates will occur in 18-48 hours.

*Lactobacillus acidophilus* NCIMB 41117 can be recovered from frozen preparations by standard culture on selective media. Briefly, bacterial cells are suspended in a small volume (1 milliliter) MRS broth (Oxoid) and serial dilutions are prepared to a dilution of 10-8. A 50 microliter aliquot of each dilution is plated onto MRS agar plates and cultures are incubated at 38 degrees centrigrade under anaerobic conditions for 18-24 h.

Since little is known regarding the cause of NSS in dogs or cats, the identification that the probiotic micro-organism deposited under the accession number NCIMB 41117 has a beneficial effect on such animals, is particularly advantageous.

In the present invention, the terms dog and cat mean the domestic dog and the domestic cat, in particular *Felis domesticus* and *Canis domesticus*.

The composition of the invention is any which a cat or dog may take. Preferably, the composition is a foodstuff. The term foodstuff covers standard food products as well as food snacks. The foodstuff may comprise a main meal product, a cereal product or confectionery, such as snack bars, biscuits and sweet products.

The foodstuff may encompass any product which a dog or a cat may consume, in particular in its diet. The foodstuff is preferably a dry pet food. Such dry pet foods include dry kibbles comprising a cooked starch source.

The foodstuff may be a cooked product. It may incorporate meat or animal derived materials (such as beef, chicken, turkey, lamb, blood plasma, marrowbone etc or two or more thereof). The composition may alternatively be meat-free (preferably including a meat substitute such as soya, maize gluten or a soya product). The composition may contain additional protein sources such as soya protein concentrate, milk proteins, gluten etc. The composition may contain a starch source such as one or more grains (e.g. wheat, corn, rice, oats, barley etc) or may be starch-free. A typical dry commercial dog and cat food contains about 30% crude protein, about 10-20% fat and the remainder being carbohydrate, including dietary fibre and ash. A typical wet or moist product contains (on a dry matter basis) about 40% fat, 50% protein and the remainder being fibre and ash. The present invention is particularly relevant for a composition as herein described which is sold as a diet, foodstuff or supplement for a cat or dog.

Further, the foodstuff may in the form of one or more of a cereal product, energy bar, breakfast cereal, confectionery, medicament, food supplement or a drink. The supplement may be in the form of a dried powder, tablet, capsule, liquid or gel.

The probiotic micro-organism may be in any form, for example in a powdered dry form or in spore form (for the micro-organisms which form spores). The probiotic may be encapsulated in order to protect it from moisture. In addition, the probiotic micro-organism may have undergone processing in order for it to increase its survival in any processing. Accordingly, the micro-organism may be coated or encapsulated in a polysaccharide, fat, starch, protein or in a sugar matrix. The probiotic micro-organism may be in a coating (outer or a layer), or a filling, or it may be admixed throughout the composition.

It may be preferable to avoid the probiotic being in contact with flour as flour contains enzymes which may adversely affect the viability of the probiotic. Standard encapsulation techniques known in the art can be used, and for example, as discussed in U.S. Pat. No. 6,190,591 (which is incorporated by reference herein).

The composition according to the first aspect of the invention may comprise the probiotic micro-organism in any concentration, preferably at a concentration of from $10^3$ to $10^{15}$ viable cells per gram of the total composition. This concentration of cells provides a suitable concentration for successful colonisation of the gastrointestinal tract and providing the optimum health benefits to the animal. An additional probiotic strain may also be present at a concentration of from $10^3$ to $10^{15}$ viable cells per gram of the total composition.

In the present text, the term "treatment" includes prophylactic treatment; that is the prevention of NSS occurring. The term "treatment" thus also includes the prophylactic treatment of an animal at risk of NSS, but not suffering from the disorder.

The present invention is particularly useful for animals which are particularly susceptible to NSS which, but are not limited to one or more dogs of the following breeds: Flat coated retriever, Irish setter, English setter, Munsterlander, Labrador, German shepherd dog, Saluki, Curly coated retriever, Belgian shepherd dog, Dalmatian, German shorthaired pointer, Weimaraner, Boxer, Poodle (standard), Afghan hound, Collie, Old English Sheepdog, English Springer Spaniel, Beagle.

A second aspect of the invention provides a method for the treatment of non-specific NSS in a cat or a dog, the method comprising administering to a cat or dog the probiotic micro-organism deposited under the accession number NCIMB 41117.

With regard to the second aspect of the invention, the preferred features of the first aspect, also apply.

According to this invention, *L. acidophilus* deposited under accession number NCIMB 41117 can stabilize the digestive processes in dogs or cats with NSS. The observed improvement in fecal consistency has considerable practical importance, since *L. acidophilus* probiotics are generally regarded as safe (GRAS status) and as such are acceptable for long-term application.

The present invention provides beneficial effects of *Lactobacillus acidophilus* deposited under accession number NCIMB 41117 on food tolerance, digestive traits and gastrointestinal microbiology in a group of dogs or cats with non-specific food sensitivity.

BRIEF DESCRIPTION OF THE DRAWINGS

The present invention is described by reference to the following FIGURE.

DETAILED DESCRIPTION OF THE INVENTION

Figure 1:
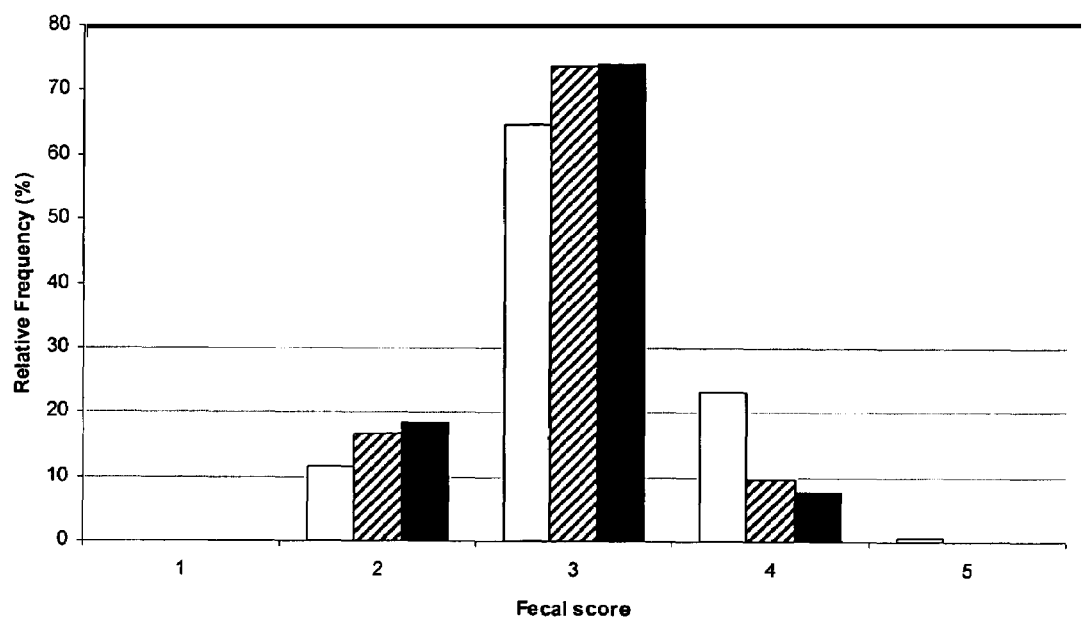
FIG. 1 shows the relative frequency of fecal scores 1-5 during each feeding period (control 1:1322 samples, probiotic: 1107 samples, control 2: 213 samples); observed frequencies differed between the dietary periods at P<0.01. ☐ Control period ▨ (single hatched box) 12 week experimental period (probiotic) ■ Subsequent control period

The present invention will now be described with reference to the following example:

Example

Material and Methods

Study design—The study design comprised 3 consecutive stages, beginning with a 12-week control period, a following 12-week experimental period (probiotic period) and a subsequent 4-week control period.

Animals—Six adult German Shorthair Pointers (4 males, 2 females, body weight 30.8±2.0 kg) with a history of non-specific dietary sensitivity were identified during a diet screening procedure. Affected dogs consistently produced feces of poor quality (loose or poorly formed) and low dry matter (DM; mean 26.2±0.93% fecal DM) compared to non-affected Beagles fed the same diet (mean 28.6±1.8% DM). All dogs were adult (2-7 years, mean 4.5) and were kept under identical conditions in a colony. Serum biochemistry was tested as part of a routine screening program and was within physiological ranges for all dogs. Stool samples were routinely investigated for parasites and all dogs were dewormed and vaccinated regularly.

Diets—The control and the probiotic diet had an identical basic nutrient profile (only the presence of the probiotic differed). The diet was a standard dry kibble foodstuff. The major ingredients were poultry meal, cereals, rice and vegetables. *Lactobacillus acidophilus* deposited under the accession number NCIMB 41117 was added to the experimental diet in a final concentration of $6 \times 10^6$ CfU/g dry dog food. All dogs were adapted to the experimental diet for 3 weeks before the initial sampling. Feed allowances were adjusted individually to achieve weight constancy (500-600 g dry diet/day). Fresh drinking water was offered ad libitum.

Assessment of fecal quality—The frequency of defecation and fecal quality was assessed daily. Trained assessors graded feces on a 1 to 5 scale, and mean feces scores were calculated for each feeding period. A grade of 1 represented dry crumbly feces and a grade of 5 represented diarrhea. Grade 2 represented feces that were well formed, easy to pick up, and left no marks. Grade 3 represented feces of good quality that were slightly moist and less well formed compared to grade 2-feces, leaving a mark when removed from a dry surface and being less consistent in texture. Grade 4-feces were of poor quality; being moist and poorly formed with a consistency characteristic of putty or porridge. Fecal dry matter was determined by oven drying (103° C. until weight constancy), while fecal unbound water was recovered by centrifugation (Sorvall RC 2B centrifuge, Bad Homburg, Germany) of 5 g feces at 47000 g for 30 min.

Assessment of the fecal microflora—Dietary effects on the intestinal microflora were investigated by culturing fecal samples for *C. perfringens, E. coli, Lactobacillus* spp. and *Bifidobacterium* spp. Briefly, 0.5 g of fresh feces was homogenized in 4.5 ml peptone water by vigorous agitation. Tenfold dilution series were produced and 100 µl volumes were cultured on selective agar plates incubated at 37° C. either aerobically for 24 h for *E. coli* (Mac Conkey agar (Oxoid, Hampshire, England)), or anaerobically for 48 h for *Lactobacillus* spp. (Man-Rogosa-Sharp agar (Sigma-Aldrich, Steinheim, Germany)), *C. perfringens* (Tryptose Sulfite Cycloserin agar (Sigma-Aldrich, Steinheim, Germany)) and *Bifidobacterium* spp. (Tomato Juice agar Becton Dickinson and Company, Sparks, USA)). Resultant bacterial colonies were counted and differentiated to the genus level. Identification was conducted on typical colonies by Gram stain and cellular morphology, for *E. coli* the indole reaction was used in addition and *Lactobacillus* spp. were characterized by biochemical fermentation profile (ApiCH050, BioMerieux Austria GmbH, Vienna, Austria). Oxidase reactions were assessed (DryOxidase-Slides, BBL Difco, Sparks, USA) and catalase activity was analysed using the hydrogen peroxide test. *Bifidobacterium* spp. and *C. perfringens* were further characterized for biochemical metabolic profiles using a commercial test kit (Rapid ID 32 A, BioMerieux Austria GmbH, Vienna, Austria).

For further investigation of the bacterial composition, in situ hybridization was performed using oligonucleotide probes (MWG Biotech, Ebersberg,Deutschland) for *E. coli* (SEQ ID NO. 1: Ecol 1531, 5'CY3-CAC CGT AGT GCC TCG TCA TCA3'), *Clostridium histolyticum* group (SEQ ID NO. 2: Chis 150, 5'CY3-AAA GGA AGA TTA ATA CCG CAT AA3'), *Bifidobacterium* spp. (SEQ ID NO. 3: Bif 164, 5'CY3-CAT CCG GCA TTA CCA CCC3') and *Lactobacillus* spp. (SEQ ID NO. 4: Lacto 158, 5'CY3-GGT ATT AGC AYC TTC CA3'). In brief, fresh feces were diluted 1:10 (w/v) in phosphate buffered saline (PBS). Bacterial cells (375 µl) within the suspension were stabilized by addition of 1.125 ml 4% (v/v) paraformaldehyde. After 24 hours the cells were harvested and washed twice in PBS, cellular material was finally suspended in 150 µl PBS and 150 µl 96% (v/v) ethanol. A 32 µl volume of the resulting solution was combined with 400 µl hybridization buffer (0.9 M NaCl, 20 mM tris(hydroxymethyl)aminomethane and 0.1% (w/v) sodium lauryl sulfate, pH 7.2) and 128 µl RNAse free water. 180 µl of the resulting hybridizing solution was added to 20 µl of the appropriate oligonucleotide probe (50 ng/µl). Hybridization was performed over 16 h for probes Chis-150, Ecol 1531 and Lacto158 at 50° C. and at 45° C. for Bif 164 in a hybridization oven (Grant Boekel HIS25, Grant Instruments Ltd., Cambridge, UK). Following hybridization, 20 µl 4',6'-diamidino-2-phenylindole-dihydrochloride (DAPI, 500 ng/ml) was added to 200 µl sample and 5 ml hybridization buffer without sodium lauryl sulfate (0.9 M NaCl, 20 mM tris(hydroxymethyl)aminomethane, pH 7.2) heated to 50° C. for 30 min for the determination of *E. coli*, *C. histolyticum*, and *bifidobacteria*. For analysis of *lactobacilli*, 900 µl hybridized sample was incubated with 20 µl DAPI for 30 min at 50° C. Samples were analyzed by vacuum filtration onto a 0.2 µm membrane filter (Carbon filter ISOPORE®,Millipore Corporation, Bedford, Mass., USA) and a commercial kit (Light Antifade Kit SLOWFADE©) was used for the stabilization of fluorescence. Membranes were stored under glass at 4° C. in the dark until investigation by fluorescence microscopy (Leitz Wetzlar, model 301-179-003, Wetzlar, Germany) under oil immersion. Counting of bacterial cells was performed with the aid of a software program (CorelDraw11© Corel, Unterschleißheim, Germany). Bacterial numbers per g feces were calculated and expressed as $\log_{10}$ counts/g feces.

Assessment of the diet composition and digestibility— Crude nutrient levels in the diets and in fecal samples were analyzed by Weende analysis (Naumann K, Bassler R. Die chemische Untersuchung von Futtermitteln, VDLUFA-*Methodenbuch III*, 5.Ergaenzungslieferung, Darmstadt: Verlag Neumann, 1993), minerals and trace elements by atomic absorption spectrophotometry (Slavin W. Atomic absorption spectroscopy. *Chem Anal* 1968; 25:87-90) and phosphorus by vanadate molybdate method (Gericke S, Kurmies B. Die kolorimetrische Phosphorbestimmung mit Ammonium-Vanadat-Molybdat und ihre Anwendung in der Pflanzenanalyse. *Z Pflanzenernahr Dung Bodenkd* 1952; 59:235-247). Digestibility studies were conducted over 5 days after a minimum of 7 adaptation days.

Statistical analysis—Data were expressed as mean±standard deviation. Comparison of the control periods and the experimental period was performed by ANOVA and Student's t-Test. Normal distribution of the data was confirmed by the Kolmogorov Smirnoff test. The Chi square test was used to compare observed and expected data distribution of fecal scores. Level of significance was $P<0.05$. All statistical analyses were performed using a software program (WinStat© R. Fitch Software, Ohio, USA) for Microsoft Excel (Microsoft©, Redmont, USA).

Results

Animals—All dogs were in good health during the study. The daily diet allowances were readily ingested and no signs of dietary intolerance were observed.

Fecal quality—The frequency of defecation ranged between 2.1-2.6/day and was slightly lower in the probiotic period (table 1). Mean fecal consistency scores were comparable between experimental periods. However, the number of fecal samples with unacceptable consistency (grades 4 and 5) was reduced during the probiotic period and persisted at a lower rate in the following control period 2 (FIG. 1). Mean fecal dry matter was 29.3±1.06% in the probiotic period compared to 26.2±0.93% in the first and 26.1±1.61% in the second control period. The percentage of unbound fecal water was reduced in the probiotic period compared to the first control period (25.5±2.26 vs. 30.9±3.22%).

TABLE 1

Number of defecations, fecal consistency, fecal dry matter and fecal unbound water in the experimental dogs in the 3 feeding periods (means ± SD)

| Diet | Defecations/day | Fecal consistency[1] | Fecal dry matter % | Fecal unbound water % |
|---|---|---|---|---|
| Control Period | 2.6 ± 0.58 | 3.5 ± 0.15 | 26.2 ± 0.93[a] | 30.9 ± 3.22[a] |
| Probiotic Period | 2.1 ± 0.38 | 3.3 ± 0.09 | 29.3 ± 1.06[b] | 25.5 ± 2.26[b] |
| Subsequent Control | 2.4 ± 0.28 | 3.4 ± 0.16 | 26.1 ± 1.61[a] | 27.5 ± 2.18[ab] |

[1]Feces were graded on a 1 to 5 scale, grade of 1 represented dry crumbly feces and grade of 5 represented diarrhea
Means within a column not sharing a common superscript are significantly different at P < 0.05 (ANOVA and post hoc t-test)

Fecal microflora—The fecal concentrations of culturable *C. perfringens*, *E. coli*, *Lactobacillus* spp. and *Bifidobacterium* spp. (table 2) were similar in all dietary periods. The concentrations of *lactobacilli* and *bifidobacteria* increased slightly, but not significantly in the probiotic period compared to both control periods.

TABLE 2

Culturable bacteria recovered from feces (log10 CfU/g; means ± SD)

| Diet | Clostridium perfringens | Escherichia coli | Lactobacillus spp. | Bifidobacterium spp. |
|---|---|---|---|---|
| Control Period | 7.92 ± 0.32 | 7.31 ± 0.27 | 8.72 ± 0.66 | 7.83 ± 1.24 |
| Probiotic Period | 7.61 ± 1.03 | 7.21 ± 0.56 | 9.26 ± 0.76 | 8.35 ± 0.81 |
| Subsequent Control | 7.98 ± 0.31 | 6.72 ± 0.69 | 8.91 ± 0.95 | 8.00 ± 0.41 |

The fecal bacterial populations as determined by in situ hybridization (table 3) were higher compared to data obtained by fecal culture and differences between dietary periods were small. However, the increase of culturable *bifidobacteria* observed during the probiotic period was confirmed by in situ hybridization.

TABLE 3

Bacterial numbers in feces as determined by in situ hybridization (log10 CfU/g; means ± SD)

| | Clostridium histolyticum group | Escherichia coli | Lactobacillus spp. | Bifidobacterium spp. |
|---|---|---|---|---|
| Control Period | 8.46 ± 0.25 | 8.39 ± 0.07 | 9.13 ± 0.06 | 8.37 ± 0.04 |
| Probiotic Period | 8.34 ± 0.05 | 8.58 ± 0.06 | 9.28 ± 0.07 | 8.75 ± 0.05 |
| Subsequent Control | 8.46 ± 0.06 | 8.57 ± 0.09 | 9.43 ± 0.07 | 8.26 ± 0.03 |

Apparent digestibility of the experimental diets—The apparent digestibilities of most organic nutrients were higher when the experimental diet was fed compared to control period 1. A trend towards higher apparent digestibilities was also seen in control period 2 compared to the baseline (table 4).

TABLE 4

Apparent digestibilities (% of intake) of dry matter, organic matter and crude nutrients in the experimental dogs in the 3 feeding periods (means ± SD)

| | Apparent digestibilities (% of intake) | | | | | |
|---|---|---|---|---|---|---|
| Diet | Dry matter | Organic matter | Crude protein | Crude fat | Crude fibre | Nitrogen free extracts |
| Control Period | 79.6 ± 3.4$^a$ | 84.5 ± 2.5 | 78.1 ± 3.5$^a$ | 90.3 ± 1.9$^a$ | 7.1 ± 16.0 | 90.1 ± 2.0 |
| Probiotic Period | 84.1 ± 2.8$^b$ | 87.2 ± 2.8 | 83.7 ± 2.6$^b$ | 93.2 ± 1.4$^b$ | 17.4 ± 12.2 | 90.8 ± 2.5 |
| Subsequent Control | 83.3 ± 2.1$^b$ | 86.5 ± 1.6 | 82.2 ± 2.4$^b$ | 92.3 ± 0.6$^b$ | 11.8 ± 12.9 | 90.8 ± 1.1 |

Means within a column not sharing a common superscript are significantly different at P<0.05 (ANOVA and post hoc t-test)

Discussion

Biologically, carnivorous species are to some extent interesting due to the specific conditions in the gastrointestinal tract, which differ from the situation in other monogastric species. The intestinal bacterial community and its metabolic activities have some particularities, as high concentrations of *Clostridium* spp. in the upper and lower gastrointestinal tract and variable numbers of *bifidobacteria*. Both of these bacterial genera are subject to fluctuations, which are dependent on diet composition.

This invention demonstrates the beneficial effects of the *Lactobacillus* probiotic in dogs with NSS. Addition of *L. acidophilus* deposited under the accession number NCIMB 41117 to the commercial diet improved feces quality considerably as observed by the significant reduction of grade 4 and 5 feces (diarrhea). This improvement in fecal consistency has considerable practical importance, since *L. acidophilus* probiotics are safe and acceptable for long-term application (GRAS status). The efficacy of the probiotic *L. acidophilus* deposited under the accession number NCIMB 41117 may result from modification of the intestinal microecology and consequent effects on the gastrointestinal digestive processes. This theory is reflected in the higher apparent digestibilities of organic matter during probiotic administration.

In conclusion, the application of the probiotic strain *Lactobacillus acidophilus* deposited under the accession number NCIMB 41117 induced a reduction in undesirable unformed feces in a group of dogs with NSS.

What is claimed is:

1. A method for the treatment of non-specific dietary sensitivity (NSDS) in a cat or a dog, the method comprising the step of administering to said cat or dog, an effective amount of the probiotic micro-organism deposited under the accession number NCIMB 41117 to treat the NSDS in the cat or the dog.

2. The method of claim 1, wherein the probiotic is part of a foodstuff.

3. The method of claim 1, wherein the probiotic micro-organism is present in the foodstuff at a range of from $10^3$ to $10^{15}$ viable cells per gram of foodstuff.

4. The method of claim 1, wherein the foodstuff is a dry, wet or semi-moist product.

5. The method of claim 1, wherein the dog is selected from the group consisting of Flat coated retriever, Irish setter, English setter, Munsterlander, Labrador, German shepherd dog, Saluki, Curly coated retriever, Belgian shepherd dog, Dalmatian, German shorthaired pointer, Weimaraner, Boxer, Poodle (standard), Afghan hound, Collie, Old English Sheepdog, English Springer Spaniel, and Beagle.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Escherichia coli

<400> SEQUENCE: 1
caccgtagtg cctcgtcatc a                                              21

<210> SEQ ID NO 2
<211> LENGTH: 23
<212> TYPE: DNA
<213> ORGANISM: Clostridium histolyticum

<400> SEQUENCE: 2
aaaggaagat taataccgca taa                                            23

<210> SEQ ID NO 3
<211> LENGTH: 18
<212> TYPE: DNA
<213> ORGANISM: Bifidobacterium sp.

<400> SEQUENCE: 3
catccggcat taccaccc                                                  18

<210> SEQ ID NO 4
<211> LENGTH: 17
<212> TYPE: DNA
<213> ORGANISM: Lactobacillus sp.

<400> SEQUENCE: 4
ggtattagca ycttcca                                                   17